United States Patent [19]

Ball et al.

[11] Patent Number: 4,492,773

[45] Date of Patent: Jan. 8, 1985

[54] PROCESS FOR THE PRODUCTION OF $C_1$ TO $C_4$ OXYGENATED HYDROCARBONS BY THE CATALYTIC CONVERSION OF SYNTHESIS GAS

[75] Inventors: William J. Ball, Capel; Leonard Cotton; David G. Stewart, both of Epsom, all of England

[73] Assignee: The British Petroleum Company Limited, London, England

[21] Appl. No.: 447,783

[22] Filed: Dec. 8, 1982

Related U.S. Application Data

[63] Continuation of Ser. No. 285,409, Jul. 20, 1981, abandoned.

[30] Foreign Application Priority Data

Aug. 1, 1980 [GB] United Kingdom ................. 8025261

[51] Int. Cl.³ ............................................. C07C 27/06
[52] U.S. Cl. .................................. 518/713; 518/714; 518/716
[58] Field of Search .................. 518/713, 714, 716

[56] References Cited

U.S. PATENT DOCUMENTS 3,957,857 5/1976 Pruett et al. .
4,162,262 7/1979 Ellgen et al. .
4,235,798 11/1980 Bartley et al. .

FOREIGN PATENT DOCUMENTS 10295 4/1980 European Pat. Off. .

OTHER PUBLICATIONS

Bhasin et al., J. of Catalysis, 54, 120–128, (1978).

*Primary Examiner*—Howard T. Mars
*Attorney, Agent, or Firm*—Brooks, Haidt, Haffner & Delahunty

[57] ABSTRACT

$C_1$ to $C_4$ oxygenated hydrocarbons are produced by contacting synthesis gas at a temperature in the range 150° C. to 450° C. and a pressure in the range of 1 to 700 bars with a catalyst comprising a supported mixture of a rhodium component and a silver component. The preferred support is silica. Other metal components which may be incorporated on the support are iron, manganese, molybdenum, tungsten, ruthenium, chromium, thorium and zirconium. Furthermore the support can be activated prior to incorporation of the metal components.

13 Claims, 1 Drawing Figure

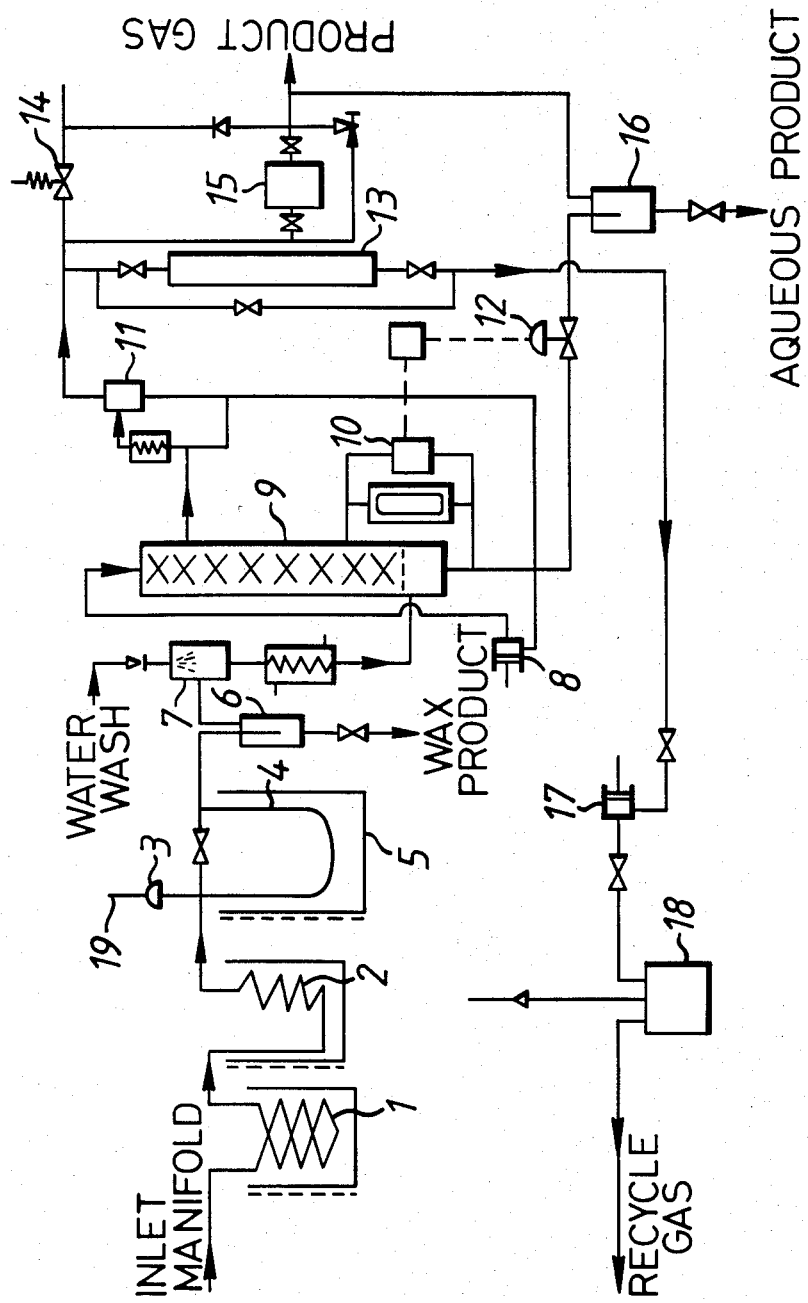

PROCESS FOR THE PRODUCTION OF $C_1$ TO $C_4$ OXYGENATED HYDROCARBONS BY THE CATALYTIC CONVERSION OF SYNTHESIS GAS

This is a continuation of application Ser. No. 285,409, filed July 20, 1981, now abandoned.

The present invention relates generally to a process for the production of $C_1$ to $C_4$ oxygenated hydrocarbon compounds such as acids, alcohols and/or aldehydes by the catalytic conversion of carbon monoxide and hydrogen mixtures, hereinafter to be referred to as synthesis gas.

$C_2$ oxygenated hydrocarbons such as acetic acid, ethanol and acetaldehyde are valuable industrial products. On a commercial scale acetic acid is generally produced either by oxidation of paraffinic hydrocarbon fractions or by carbonylation of methanol; ethanol is produced either by fermentation of natural products, e.g. molasses or by hydration of ethylene in the presence of an acid catalyst; acetaldehyde is produced by the oxidation of ethanol or by direct oxidation of ethylene as in the Wacker process. $C_3$ and $C_4$ acids, alcohols and aldehydes are produced from petrochemical feedstocks by similar processes involving oxidation, hydroformylation, hydrogenation and hydration. The dwindling reserves of crude oil from which many of the above feedstocks are derived and the associated need to utilise fully the remaining natural resources such as coal and the vast amounts of gases e.g. methane potentially available from the exploitation of North Sea oilfields, has stimulated research into the utilisation of synthesis gas, which can readily be obtained not only from crude oil but also from both coal and methane gas. Much of the early work on synthesis gas conversion involved the use as catalysts of the metals of Group VIII of the Periodic Table such as iron, cobalt, nickel and ruthenium and various other metal oxide systems. One general disadvantage of such systems is that catalysts which possess acceptable activity generally tend to be unselective i.e. they produce a wide spectrum of products including both hydrocarbons and oxygenated hydrocarbons having a very broad distribution of carbon numbers. This not only complicates the recovery of the desired products but also results in the wastage of reactants to undesirable products. On the other hand those catalysts having acceptable selectivity generally have a low activity thereby necessitating recycle of large quantities of unchanged reactants.

In published Netherlands application No. 7500916 there is disclosed a process which, it is claimed, overcomes the aforesaid disadvantages of the prior art processes. The process for selectively producing $C_2$ oxygenated hydrocarbons involves continuously contacting synthesis gas with a heterogeneous catalyst essentially comprising rhodium metal under reaction conditions correlated so as to favour the formation of a substantial proportion of acetic acid, ethanol and/or acetaldehyde. Subsequent patent applications describe the production of ethanol and/or acetic acid by contacting synthesis gas with a rhodium/iron catalyst published Netherlands application No. 7500918), a rhodium/manganese catalyst (DT No. 2,628,463), a rhodium/molybdenum or rhodium/tungsten catalyst (U.S. Pat. No. 4,096,164), a rhodium/ruthenium catalyst (U.S. Pat. No. 4,101,450), and a rhodium/uranium/thorium catalyst (U.S. Pat. No. 4,162,262). European application No. 80301284.8 describes the use of a rhodium/chromium catalyst for the production of $C_1$ to $C_4$ oxygenated hydrocarbons. U.K. Application No. 79/40844 describes the use of a rhodium/zirconium catalyst for the production of $C_2$ oxygenated hydrocarbons and U.K. application No. 80/20959 describes the use of a rhodium/rhenium catalyst for the production of a methanol/ethanol mixture.

It has now been found that a supported mixture of a rhodium component and a silver component is an active catalyst for the selective production of oxygenated hydrocarbon compounds containing from one to four carbon atoms.

Accordingly the present invention provides a process for the production of $C_1$ to $C_4$ oxygenated hydrocarbon compounds which process comprises contacting synthesis gas at a temperature in the range 150° to 450° C. and a pressure in the range 1 to 700 bars with a catalyst comprising a supported mixture of a rhodium component and a silver component.

Mixtures of the gases hydrogen and carbon monoxide are abundantly available in the form of synthesis gas. Methods for preparing synthesis gas are well-known in the art and usually involve the partial oxidation of a carbonaceous substance, e.g. coal. Alternatively synthesis gas may be prepared, for example, by the catalytic steam reforming of methane. Although it is preferred to use substantially pure synthesis gas the presence of such impurities as carbon dioxide and nitrogen can be tolerated. On the other hand impurities which have a deleterious effect on the reaction should be avoided. The ratio of hydrogen to carbon monoxide in the synthesis gas may vary widely. Normally the molar ratio of hydrogen to carbon monoxide may be in the range of from 20:1 to 1:20, preferably from 5:1 to 1:5. Methods for adjusting the molar ratio of hydrogen to carbon monoxide by the so-called 'shift reaction' are well-known to those versed in the art.

The catalyst comprises a supported mixture of a rhodium component and a silver component. A wide variety of support materials may be employed. Suitable support materials include silica, alumina, silica/alumina, magnesia, thoria, titania, chromia, zirconia and active carbon, of which silica is preferred. Zeolite molecular sieves and in particular the crystalline zeolites may also be employed. Suitably the support has a relatively high surface area. The support may have a surface area up to 350 square meters per gram (BET low temperature nitrogen adsorption isotherm method), preferably in the range 1 to 300 square meters per gram. Whilst the actual form of the rhodium and silver components under the reaction conditions is not known with any degree of certainty it is likely that they are in either the oxide form or in the metallic form under the reducing conditions prevailing. Thus the rhodium and silver components may be added in the form of the metals themselves or in the form of metal compounds and may be added concurrently or sequentially. The rhodium and silver components may be deposited on the support by any of the techniques commonly used for catalyst preparation. Although it is possible to add particles of the metals to the support it is preferred to use the techniques of impregnation from an organic or inorganic solution, precipitation, coprecipitation or cation exchange. Conveniently the catalyst may be prepared by impregnating the support with a solution of an inorganic or organic rhodium and silver compound. Suitable compounds are the salts of the metals e.g. the halides, particularly the chlorides and nitrates. Following impregnation the catalyst is preferably dried and calcined. The amount of each of the rhodium component and the silver component on the support may suitably be in the range of from 0.01 to 25 weight percent, preferably from 0.1 to 10 weight percent, based on the combined weight of the metals and the support. The catalyst may be further improved by incorporating on the support one or more other metal components selected from iron, manganese, molybdenum, tungsten, ruthenium, chromium, thorium, and zirconium. Each additional metal component may be present in an amount in the range from 0.1 to 10 weight percent based on the combined weight of the metals and the support.

In another embodiment of the present invention the support can be activated by the addition of one or more metal or non-metal activator components followed by calcination prior to incorporation of the rhodium and silver components and, optionally, other metals. Whilst a wide variety of such metals and non-metals may be added, the alkali metals, thorium, manganese, rhodium, iron, chromium, molybdenum, zirconium, rhenium, silver, boron and phosphorus are specific examples of such materials. Any of the known techniques for catalyst preparation hereinbefore referred to may be used for addition of the activating material. In the case of a metal activator the support is preferably impregnated with a solution of a compound of the metal, suitably the nitrate or chloride, and is thereafter dried, suitably by evaporation and calcined. The activated support is then in a suitable condition for addition of the activating material. In the case of a metal activator the support is preferably impregnated with a solution of a compound of the metal, suitably the nitrate or chloride, and is thereafter dried, suitably by evaporation and calcined. The activated support is then in a suitable condition for addition of the rhodium and silver components. The amount of activator component added may suitably be in the range 0.01 to 50 weight percent, preferably from 1 to 25 weight percent based on the combined weight of the activator component and the support.

With regard to the reaction conditions the temperature is preferably in the range from 200° to 400° C. and even more preferably from 220° to 350° C.; the use of higher temperatures within the aforesaid ranges tends to increase the co-production of methane. Because of the highly exothermic nature of the reaction the temperature requires careful control in order to prevent a runaway methanation, in which methane formation increases with increasing temperature and the resulting exotherm increases the temperature still further. In fixed bed operations, temperature control may be achieved by mixing the catalyst with an inert diluent, thereby ensuring that the exothermic heat is more evenly distributed. In this way the useful life of the catalyst may be protected and prolonged. The reaction pressure is preferably in the range from 20 to 300 bars. The use of higher pressures within the aforesaid ranges increases the production rate and selectivity to $C_1$ to $C_4$ oxygenated hydrocarbons.

An important reaction parameter is the conversion. A low conversion, preferably less than 20% of the carbon monoxide, favours the formation of the lower acids, alcohols and aldehydes. A low conversion may suitably be achieved in a continuous process by employing a high space velocity. Suitably the gas hourly space velocity (volume of synthesis gas, at STP, per volume of catalyst per hour) is greater than $10^3$ per hour, preferably the gas hourly space velocity is in the range from $10^4$ to $10^6$ per hour. Excessively high space velocities result in an uneconomically low conversion while excessively low space velocities result in a loss of selectivity to desirable products.

Although the reaction may be carried out batchwise it is preferably carried out in a continuous manner.

The catalyst may be employed in the form of a fixed or a fluidised bed.

The effluent from the reaction may be freed from the desired oxygenated products by various means, such as scrubbing and/or distillation. The residual gas which consists mainly of unreacted synthesis gas may be mixed with fresh carbon monoxide and hydrogen to give the required reactor feed and this composite gas then recycled to the reactor inlet.

The process of the invention will now be illustrated by the following Examples and by reference to the accompanying FIGURE which is a simplified flow diagram of the apparatus employed.

With reference to the FIGURE, 1 is a preheater (150° C.), 2 is a preheater (200° C.), 3 is a bursting disc, 4 is a reactor, 5 is a salt pot, 6 is a knock-out pot, 7 is a water quench, 8 is a water recycle pump, 9 is a water wash tower, 10 is a DP level controller, 11 is a knock-out pot, 12 is a Foxboro valve, 13 is a molecular sieve drier, 14 is a Gyp relief valve, 15 is a back pressure regulator, 16 is an aqueous product receiver, 17 is a gas recycle pump, 18 is a ballast vessel and 19 is a vent.

Also in the Examples the terms CO conversion and selectivity will be used. For the avoidance of doubt these are defined as follows:

$$CO\ \text{Conversion} = \frac{\text{Moles of carbon monoxide consumed}}{\text{Moles of carbon monoxide fed}} \times 100$$

$$\text{Selectivity} = \frac{\text{Moles of carbon monoxide converted to particular product}}{\text{Moles of carbon monoxide consumed.}} \times 100$$

CATALYST PREPARATION

Catalyst A (silver/rhodium/silica)

Silver nitrate (0.9 g) was dissolved in deionised water (25 ml) and the solution added to Davison silica, grade 59 (10 g, 8–16 mesh granules). The mixture was evaporated to dryness on a steam-bath.

Rhodium trichloride trihydrate (1.3 g) was dissolved in deionised water (25 ml) and the resulting solution added to the above support. The mixture was evaporated to dryness on a steam-bath, dried at 120° C. for 16 hours and the catalyst reduced by heating at 450° C. in hydrogen for 2 hours at atmospheric pressure and then for 6 hours under a pressure of 4 bars.

Catalyst B (silver/gold/rhodium/silica)

Chloro-auric acid (1.0 g, containing 51% gold) and rhodium trichloride trihydrate (1.3 g) were dissolved in deionised water (20 ml) and the solution added to Davison silica, grade 59 (10 g, 8–16 mesh granules). The mixture was evaporated to dryness on a steam-bath and the dry product reduced in hydrogen at 450° C. for 6 hours.

Silver nitrate (0.9 g) was dissolved in deionised water (20 ml) and the resulting solution added to the above support. The mixture was evaporated to dryness and the solid further dried at 120° C. for 16 hours and then reduced by heating at 450° C. in hydrogen for 6 hours at atmospheric pressure.

Catalyst C (silver/copper/rhodium/silica)

Rhodium trichloride trihydrate (1.3 g) was dissolved in deionised water (20 ml) and the resulting solution added to Davison silica, grade 59 (10 g, 8–16 mesh granules). The mixture was evaporated to dryness on a steam-bath and the dry product reduced in hydrogen at 450° C. for 3 hours.

Silver nitrate (0.9 g) and copper nitrate trihydrate (0.76 g) were dissolved in deionised water (20 ml) and the resulting solution was added to the above support. The mixture was evaporated to dryness and the catalyst dried at 120° C. and then reduced by heating in hydrogen for 6 hours at atmospheric pressure.

Catalyst D (silver/molybdenum/rhodium/silica)

Rhodium trichloride trihydrate (1.3 g) was dissolved in deionised water (20 ml) and the resulting solution added to Davison silica (10 g, 8–16 mesh granules). The mixture was evaporated to dryness on a steam bath and the solid dried at 120° C. and then reduced in hydrogen at 450° C. for 6 hours.

Silver nitrate (0.9 g) was dissolved in deionised water (20 ml) and the solution added to the above solid. The mixture was evaporated to dryness on a steam bath and the solid dried at 120° C. and then reduced in hydrogen at 450° C. for 6 hours.

Ammonium heptamolybdate tetrahydrate (0.42 g) was dissolved in deionised water (20 ml) and the resulting solution was added to the above support and the whole was evaporated to dryness on a steam-bath. The catalyst was dried at 120° C. and then reduced at 450° C. in hydrogen for 6 hours.

Catalyst E (silver/molybdenum/potassium/rhodium/silica)

Silver nitrate (0.9 g) was dissolved in deionised water (20 ml) and the resulting solution added to Davison silica, grade 59 (10 g, 8–16 mesh granules). The mixture was evaporated to dryness on a steam bath and the solid dried at 120° C. and then reduced in hydrogen at 450° C. for 4 hours.

Rhodium trichloride trihydrate (1.3 g) was dissolved in deionised water (20 ml) and the resulting solution added to the above solid. The mixture was evaporated to dryness on a steam-bath and the solid dried at 120° C. and then reduced in hydrogen at 450° C. for 4 hours.

Ammonium heptamolybdate tetrahydrate (0.42 g) was dissolved in deionised water (20 ml) and the resulting solution added to the above solid. The mixture was evaporated to dryness on a steam-bath and the solid dried at 120° C. and then reduced in hydrogen at 450° C. for 4 hours.

Potassium acetate (0.06 g) was dissolved in deionised water (20 ml) and the resulting solution was added to the above solid. The mixture was evaporated to dryness on a steam-bath and the catalyst dried at 120° C. and reduced in hydrogen at 450° C. for six hours.

Catalyst F (silver/zinc/rhodium/silica)

Rhodium trichloride trihydrate (1.3 g) was dissolved in deionised water (20 ml) and the resulting solution added to Davison silica, grade 59 (10 g, 8–16 mesh granules). The mixture was evaporated to dryness on a steam-bath and the solid dried at 120° C. and then reduced in hydrogen at 450° C. for 3 hours.

Silver nitrate (0.9 g) and zinc nitrate tetrahydrate (0.8 g) were dissolved in deionised water (20 ml) and the resulting solution added to the above solid. The mixture was evaporated to dryness on a steam bath and the catalyst dried at 120° C. and reduced at 450° C. in hydrogen for 6 hours.

Catalyst G (silver/rhodium/zirconia)

Zirconium nitrate (60 g) was dissolved in deionised water (1 liter) and aqueous ammonia solution (910 ammonia:water=1:1) was added slowly with stirring until the pH was 8. The mixture was filtered and the precipitate washed three times by resuspension in deionised water (3×1 liter) and finally dried at 120° C. for 16 hours. The zirconium oxide was ground to pass 100 mesh (B.S.S.) and washed with N-sulphuric acid on a filter paper (30 ml of acid to 2 g of zirconium oxide). The acid treated oxide was then calcined at 630° C. in air for 3 hours.

Rhodium trichloride trihydrate (1.3 g) was dissolved in deionised water and the resulting solution was added to the treated zirconium oxide (32.8 g). The mixture was evaporated to dryness on a steam-bath and the solid dried at 120° C. and reduced in hydrogen at 450° C. for 6 hours.

Silver nitrate (0.9 g) was dissolved in deionised water (20 ml) and the resulting solution added to the above solid and the whole evaporated to dryness on a steam bath. The catalyst was dried at 120° C. and reduced at 450° C. for 6 hours in hydrogen.

CATALYST TESTING

Example 1

With reference to the accompanying FIGURE a mixture of carbon monoxide and hydrogen in a molar ratio of 1:2 was passed via the inlet manifold through the two preheater coils (1) and (2) maintained at 150° C. and 200° C. respectively in silicone oil baths. The heated gases were then fed via a heat-traced line to the copper liner reactor (4) which was maintained at 50 bars pressure and contained a fixed bed of the silver/rhodium/silica catalyst (Catalyst A), in the form of 8 to 16 mesh (BSS) granules. The reactor was maintained at the desired reaction temperature by immersion in a molten salt bath (5). The product gases were passed via a heat-traced line through a knock-out pot for wax products (6) to a small quench vessel (7) into the top of which water was sprayed. The gases were then passed through a water cooler to the bottom of the water wash tower (9) which was packed with ⅜ inch Raschig rings. In the tower (9) the product gases were washed counter-current with water. The resulting liquid product was fed into the receiver (16) and any dissolved gases were recombined with the product gas stream from the back pressure regulator (15). The separated gas stream from the top of the water wash tower (9) was passed through a water cooler to the knock-out pot (11) and then to the inlet side of the dome-loaded back pressure regulator (15). Recycle gas was recovered from the inlet side of the back pressure regulator (15), passed through a molecular sieve drier (13) and compressed up to 67 bars in the gas ballast vessel (18) using the gas recycle pump (17). The recycle gas was fed back to the inlet manifold. Provision was made to feed spot samples of the inlet gases and the total gas stream to a gas chromatographic analytical unit.

The product gas stream leaving the back pressure regulator (15) was measured and samples were withdrawn and analysed by gas chromatography. The liquid product was also sampled and analysed by gas chromatography.

When the reactor had reached equilibrium a balanced run was carried out over a one hour period.

Example 2

The procedure of Example 1 was repeated except that Catalyst A was replaced by Catalyst B and the temperature was 345° C.

Example 3

The procedure of Example 1 was repeated except that Catalyst A was replaced by Catalyst C and the temperature was 355° C.

Example 4

The procedure of Example 1 was repeated except that Catalyst A was replaced by Catalyst D and the temperature was 270° C.

Example 5

The procedure of Example 1 was repeated except that Catalyst A was replaced by Catalyst E and the temperature was 350° C.

Example 6

The procedure of Example 1 was repeated except that Catalyst A was replaced by Catalyst F and the temperature was 400° C.

Example 7

The procedure of Example 1 was repeated except that Catalyst A was replaced by Catalyst G and the temperature was 345° C.

The reaction conditions and results for Examples 1 to 7 are given in the accompanying Table.

We claim:

1. A process for the production of $C_1$ to $C_4$ oxygenated hydrocarbon compounds comprising methanol and/or ethanol which process comprises contacting synthesis gas at a temperature in the range of from 150° to 450° C. and a pressure in the range of from 1 to 700 bars with a catalyst comprising a mixture of a rhodium component and a silver component on the same support, said rhodium and silver components under the reaction conditions being substantially in the metallic form.

2. A process according to claim 1 wherein the molar ratio of hydrogen to carbon monoxide in the synthesis gas is in the range from 5:1 to 1:5.

3. A process according to either claim 1 or claim 2 wherein the support is silica, alumina, silica/alumina, magnesia, thoria, titania, chromia, zirconia, active carbon or a zeolite molecular sieve.

4. A process according to claim 3 wherein the support has a surface area in the range 1 to 300 square meters per gram.

5. A process according to claim 1 wherein the catalyst also contains molybdenum and the support is silica.

6. A process as defined in claim 1 wherein the pressure is from 20 to 300 bars.

7. A process according to claim 3 wherein the support is silica.

8. A process according to claim 3 wherein there is also incorporated on the support one or more other metal components selected from iron, manganese, molybdenum, tungsten, ruthenium, chromium, and thorium.

9. A process according to claim 3 wherein, prior to the addition of the rhodium and silver components of the catalyst, the support is activated by the addition of one or more metals and non-metals selected from the alkali metals, thorium, manganese, iron, chromium, molybdenum, rhenium, boron and phosphorus, followed by calcination.

10. A process according to claim 3 wherein the temperature is in the range 200° to 400° C.

11. A process according to claim 3 wherein the pressure is in the range 20 to 300 bars.

12. A process according to claim 3 wherein the conversion is less than 20 mole % of the carbon monoxide.

13. A process according to claim 3 when operated continuously at a gas hourly space velocity in the range $10^4$ to $10^6$ per hour.

TABLE

| | | Reaction Parameters: | | | | | GHSV = 50 000 $H_2$: CO molar ratio = 2:1 Pressure = 50 bars Recycle gas ratio = 20:1 | | | | |
| | | Reaction Temperature °C. | CO Conversion % | | | | Selectivity % | | | | |
| Example | Catalyst | | | Carbon dioxide | Methane | Ethane | Methanol | Ethanol | n-Propanol | Acetaldehyde | Acetic Acid |
| --- | --- | --- | --- | --- | --- | --- | --- | --- | --- | --- | --- |
| 1 | A | 310 | 11 | 2 | 33 | 3 | 11 | 30 | 3 | 14 | 4 |
| 2 | B | 345 | 20 | 2 | 47 | 4 | 16 | 22 | 2 | 7 | — |
| 3 | C | 355 | 6 | 2 | 36 | 1 | 41 | 20 | — | — | — |
| 4 | D | 270 | 44 | 2 | 25 | 5 | 47 | 17 | 3 | — | 1 |
| 5 | E | 350 | 33 | 2 | 50 | 12 | 17 | 16 | 3 | — | — |
| 6 | F | 400 | 22 | 1 | 44 | 11 | 32 | 10 | 2 | — | — |
| 7 | G | 345 | 15 | 23 | 35 | 10 | 19 | 13 | — | — | — |

* * * * *